(12) United States Patent
Tseng et al.

(10) Patent No.: US 11,080,934 B2
(45) Date of Patent: Aug. 3, 2021

(54) MIXED REALITY SYSTEM INTEGRATED WITH SURGICAL NAVIGATION SYSTEM

(71) Applicant: National Central University, Taoyuan (TW)

(72) Inventors: Ching Shiow Tseng, Taoyuan (TW); Te-Hsuan Feng, Taoyuan (TW)

(73) Assignee: National Central University, Taoyuan (TW)

( * ) Notice: Subject to any disclaimer, the term of this patent is extended or adjusted under 35 U.S.C. 154(b) by 13 days.

(21) Appl. No.: 16/690,299

(22) Filed: Nov. 21, 2019

(65) Prior Publication Data
US 2021/0065451 A1    Mar. 4, 2021

(30) Foreign Application Priority Data

Aug. 30, 2019 (TW) .................................. 108131367

(51) Int. Cl.
*G06T 19/00* (2011.01)
*G06T 7/73* (2017.01)
(Continued)

(52) U.S. Cl.
CPC ............ *G06T 19/006* (2013.01); *A61B 34/20* (2016.02); *A61B 34/30* (2016.02); *A61B 90/37* (2016.02);
(Continued)

(58) Field of Classification Search
CPC ......... G06T 19/006; G06T 7/174; G06T 7/73; G06T 2207/30244; G06T 2207/30101; G06T 2207/30204; G06T 2210/41; A61B 34/30; A61B 34/20; A61B 90/39; A61B 90/37; A61B 2090/3945; A61B 2034/2051; A61B 2034/2048; A61B 2034/2055; A61B 2090/3958; A61B 2090/365

See application file for complete search history.

(56) References Cited

U.S. PATENT DOCUMENTS

2017/0258526 A1* 9/2017 Lang ...................... A61B 34/74
2018/0071032 A1* 3/2018 de Almeida Barreto .................... A61B 34/10

(Continued)

*Primary Examiner* — Grace Q Li
(74) *Attorney, Agent, or Firm* — Demian K. Jackson; Jackson IPG PLLC

(57) ABSTRACT

The present invention relates to a mixed reality system integrated with a surgical navigation system including a group of moveable position markers configured on a surgical instrument; a position sensor sensing the group of moveable position markers to acquire an instrument coordinate for the surgical instrument; a registered positioning marker configured in proximity to a surgical area to acquire a surgical area coordinate for the surgical area; a plurality of mixed reality sensors detecting the registered positioning marker and a plurality of mixed reality information; a computing unit module configured to receive the instrument coordinate, the surgical area coordinate, the plurality of mixed reality information, and a digital model of the surgical area, to render the digital model corresponded to the surgical area, and to add a digital instrument object into the digital model in accordance with the instrument coordinate; and a mixed reality display providing for a user to view and showing the digital model and the digital instrument object to the user upon the receipt thereof.

10 Claims, 12 Drawing Sheets

(51) Int. Cl.
*A61B 34/20* (2016.01)
*A61B 34/30* (2016.01)
*A61B 90/00* (2016.01)
*G06T 7/174* (2017.01)

(52) U.S. Cl.
CPC .............. *A61B 90/39* (2016.02); *G06T 7/174* (2017.01); *G06T 7/73* (2017.01); *A61B 2034/2048* (2016.02); *A61B 2034/2051* (2016.02); *A61B 2034/2055* (2016.02); *A61B 2090/365* (2016.02); *A61B 2090/3945* (2016.02); *A61B 2090/3958* (2016.02); *G06T 2207/30101* (2013.01); *G06T 2207/30204* (2013.01); *G06T 2207/30244* (2013.01); *G06T 2210/41* (2013.01)

(56) References Cited

U.S. PATENT DOCUMENTS

| | | | |
|---|---|---|---|
| 2018/0182150 A1* | 6/2018 | Benishti | H04N 13/383 |
| 2019/0254754 A1* | 8/2019 | Johnson | G16H 40/63 |

\* cited by examiner

HX ated August 30, filed in Taiwan intellectual property office.
MIXED REALITY SYSTEM INTEGRATED WITH SURGICAL NAVIGATION SYSTEM

CROSS-REFERENCE TO RELATED APPLICATION

The present application claims the priority benefit of Taiwan invention patent application Ser. No. 108131367, dated August 30, filed in Taiwan intellectual property office. All contents disclosed in the above Taiwan invention patent application is incorporated herein by reference.

FIELD

The present invention relates to a mixed reality system, in particular to a mixed reality system integrated with a surgical navigation system utilizing multiple moveable position markers and a positioning marker to enable a correspondence and alignment between a digital virtual image model and a surgical area in the reality.

BACKGROUND

In the state of the art, processes to treat cerebral aneurysm in a conventional craniotomy are able to describe as follows: the patient's scalp is first incised, several small holes are drilled through the patient's skull right above the surgical area for cerebral aneurysm, then the patient's cranium is sawn off and the incised cranium is moved away. Afterwards, under a guidance from a computer assisted surgical navigation system, various types of surgical instruments are applied to go through and flip off layer upon layer of brain tissues to find out the cerebral aneurysm, while X-ray is continuously used to verify the location of the instruments in relation to the brain tissues. After the exact location for aneurysm is confirmed, the surgical instruments are used to clip the aneurysmal vessels. When the surgical procedures are completed, the cranium is closed and sutured. However, the conventional craniotomy has several major problems as follows.

(1) Before the operation and during the operation process, usually surgeons refer to a series of planar images from brain computer tomography (CT) scan as shown in FIG. 1, the digital subtraction angiography (DSA) images, the computed tomography angiography (CTA) images, or the maximum intensity projection (MIP) images for brain; (2) Therefore, surgeons may not be able to see the surgical area directly during the execution of craniotomy, can refer to the above types of images displayed on the surgical navigation system, and then estimate and imagine the exact location of cerebral arteries according to expertise and years' clinical experience; they need to plan the surgical path, so as to avoid injuring the cerebral arteries in the course of operation; (3) even if the present technology has been able to display the three-dimensional distribution of blood vessels of the brain, surgeons have to view the computer screen of the navigation system continuously to determine the complex branches and bending of cerebral arteries during the operation, so as to confirm the relative positions of instruments and blood vessels; (4) to ensure 100% accuracy of the location of aneurysm, surgeons must continuously watch the navigation system screen or microscopic images; (5) to avoid surgical accidents, surgeons operate surgical instruments carefully and slowly in the course of operation, open each layer of the brain tissues to approach the surgical area, and view the aforesaid images at times to confirm the location of the surgical instruments in relation to the peripheral brain tissues.

The process of the conventional aneurysmal embolization (or endovascular coiling) operation for treating cerebral aneurysm is described below: the artery at the groin is punctured up to the cerebral arteries; the direction and location of the guide wire are confirmed according to the planar real-time DSA images; after the guide wire reaches the surgical area of cerebral aneurysm, coils are implanted at the target position; then the guide wire is retrieved. Such aneurysmal embolization operation is confronted with the following problems: the X-ray image only provides two-dimensional information in the process; at the bifurcation of blood vessels, a large amount of X-ray images need to be taken in order to confirm the location of the guide wire in relation to the complex geometric shape of blood vessels, which is not only time-consuming, but also generating high radiation dose.

In order to reduce the wounds on human body and to avoid large wounds as possible, the minimally invasive surgery becomes the main trend of surgery. The minimally invasive surgery is characterized by small wounds, less blood loss, minor tissue injury, and quick postoperative recovery. For smaller surgical incision, the minimally invasive surgery has been extensively used in surgical procedures that do not require large incisions or where the large incision surgery can be replaced by minimally invasive surgery. However, the minimally invasive surgery is also confronted with the surgical risks when the surgeons are unable to see the entire surgical area directly, but only a small part of the outer tissues of surgical area. In the course of minimally invasive surgery, as the surgical incision is small, so that surgeons sometimes only see a part of tissues of the operation area. As a result, surgeons rely on the planar images and their clinical experience to analyze the blood vessels, nerves and tissue structure of the surgical area, and plan the appropriate surgical path. If the aorta is injured in the process, there will be bleeding, or serious sequelae even death of the patient.

Hence, there is a need to solve the above deficiencies/issues.

SUMMARY

In view of difficulties and insufficiencies existing in the conventional surgery, the present invention applies the advanced Mixed Reality (MR) technology to enable surgeons to see the 3D graphical digital model projected outside a patient's body projected in the patients, which the 3D graphical digital model is well aligned to the surgical area, displays dynamically, and shows human tissues, e.g. vertebrae or artery, and orientations and positions for surgical instruments, which significantly increases surgeons' confidence and surgery safety during a surgical operation.

The present invention provides a mixed reality system integrated with a surgical navigation system including: a group of moveable position markers configured on a surgical instrument; a position sensor sensing the group of moveable position markers to acquire an instrument coordinate for the surgical instrument; a registered positioning marker configured in proximity to a surgical area to acquire a surgical area coordinate for the surgical area; a plurality of mixed reality sensors detecting the registered positioning marker and a plurality of mixed reality information; a computing unit module configured to receive the instrument coordinate, the surgical area coordinate, the plurality of mixed reality information, and a digital model of the surgical area, to render the digital model corresponded to the surgical area, and to add a digital instrument object into the digital model in accordance with the instrument coordinate; and a mixed reality display providing for a user to wear and showing the digital model and the digital instrument object to the user upon the receipt thereof.

The mixed reality system further includes one of devices as follows: a C-arm imaging machine providing for forming an X-ray image, a computer tomography image, a computer tomography angiography image, a digital subtraction angiography image, a maximum intensity projection image, a diffusion tensor imaging image, a nuclear magnetic resonance imaging image, or a nuclear magnetic resonance angiography image; a computer selectively including the computing unit module; a surgical area image reconstruction module including an intelligent computing algorithm configured to execute by the computing unit module selectively to generate the digital model of the surgical area; a robot-assisted surgery equipment configured to assist the user to perform a surgery; and a display panel receiving and showing digital contents provided by the computer.

Preferably, the digital model of the surgical area is pre-constructed based on one of an X-ray image, a computer tomography image, a computer tomography angiography image, a digital subtraction angiography image, a maximum intensity projection image, a diffusion tensor imaging image, a nuclear magnetic resonance imaging image, a nuclear magnetic resonance angiography image, and a combination thereof by executing an intelligent computing algorithm, and the intelligent computing algorithm include one of a noise removal processing, a feature identification processing, a feature enhancement processing, an alignment processing, a stitch processing, in interpolation processing, an extrapolation processing, and a combination thereof.

Preferably, the digital model of the surgical area is one of a two-dimension digital image of the surgical area, a three-dimension digital image of the surgical area, and a combination thereof.

Preferably, the plurality of mixed reality sensors and the mixed reality display are configured on the same one device, or each of the plurality of mixed reality sensors and the mixed reality display are configured on separate devices respectively.

Preferably, the computing unit module, the plurality of mixed reality sensors and the mixed reality display are configured on the same one device, the computing unit module and the plurality of mixed reality sensors are configured on the same one device, the computing unit module and the mixed reality display are configured on the same one device, the computing unit module, the plurality of mixed reality sensors and the mixed reality display are configured on separate devices respectively, the computing unit module and the plurality of mixed reality sensors are configured on separate devices respectively, or the computing unit module and the mixed reality display are configured on separate devices respectively.

Preferably, the plurality of mixed reality sensors are selected from a surrounding camera, a depth camera, a light sensor, a RGB camera, an infra-ray camera, an inertia measurement unit, a multi-axis accelerometer, a rangefinder, and a combination thereof.

Preferably, the position sensor is an infra-ray tracker or an electromagnetic tracker, the group of moveable position markers is an infra-ray reflective marker or a coil winding marker and provides for configuring on the surgical instrument, and the registered positioning marker includes a two-dimension code pattern.

Preferably, the plurality of mixed reality sensors and the mixed reality display are configured on the same one mixed reality device, and the mixed reality device is a Microsoft Hololens device, an ODG R-7 smart glass, an Epson Moverio BT-300 smart glass, or an Acer mixed reality glass.

The mixed reality system in Embodiment 1 further includes one of devices as follows: a registered device configured in proximity to a surgical area and having a first surface and a second surface fixed with the first surface wherein the first surface provides for the positioning marker to configure and the second surface provides for the group of moveable position markers to configure, and while the registered device is placed the relative positions of the positioning marker and the group of moveable position markers with respect to the surgical area are determined accordingly; and a platform configured in proximity to a surgical area and having a plurality of surfaces wherein one of the plurality of surfaces provides for the group of moveable position markers to configure and the others of the plurality of surfaces provides for a plurality of the positioning markers to configure, and while the platform is placed the relative positions of the plurality of the positioning markers and the group of moveable position markers with respect to the surgical area are determined accordingly.

DESCRIPTION OF THE DRAWINGS

A more complete appreciation of the invention and many of the attendant advantages thereof are readily obtained as the same become better understood by reference to the following detailed description when considered in connection with the accompanying drawing, wherein.

DETAILED DESCRIPTION

Figure 1:
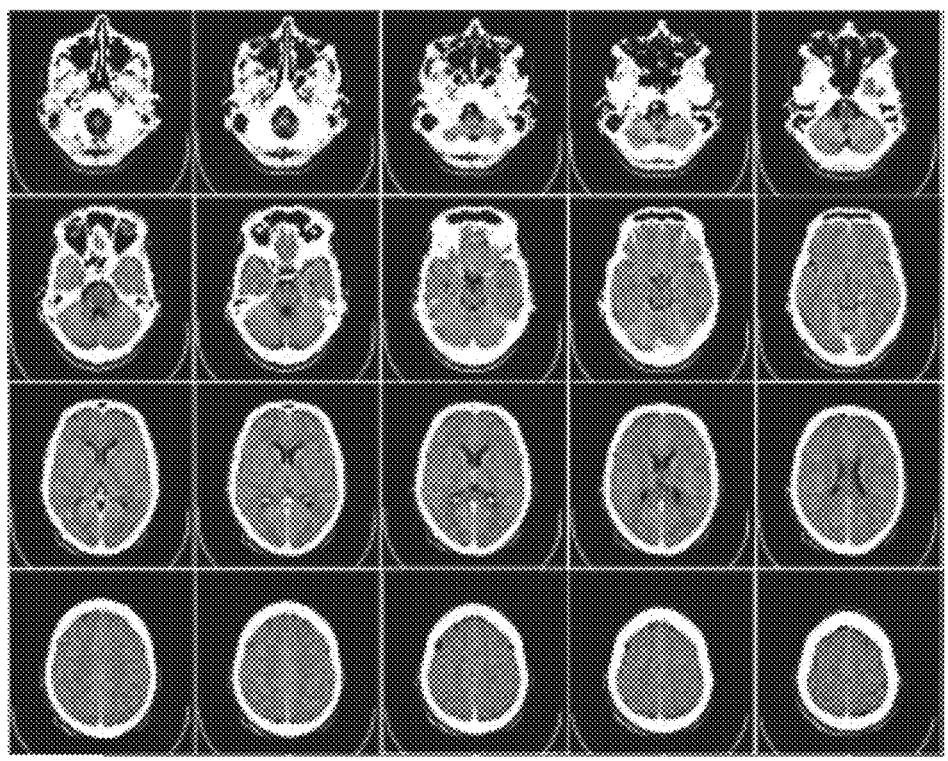
FIG. 1 is a diagram illustrating a series of 2D computer tomography slice images on an axial plane for a brain in the prior art.

The present disclosure will be described with respect to particular embodiments and with reference to certain drawings, but the disclosure is not limited thereto but is only limited by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice.

It is to be noticed that the term "including", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device including means A and B" should not be limited to devices consisting only of components A and B.

The disclosure will now be described by a detailed description of several embodiments. It is clear that other embodiments can be configured according to the knowledge of persons skilled in the art without departing from the true technical teaching of the present disclosure, the claimed disclosure being limited only by the terms of the appended claims.

The mixed reality (MR) described in the present invention refers to the technology which uses precise calculation of location and angle of camera image, as well as image analysis technique, in combination and interaction with the virtual digital content on the screen and the real scenes. Virtual digital objects viewed by a user and displayed on the screen of the MR device, are correspondingly and accurately superposed and projected to actual articles, instruments, devices, or a surgical area in reality world where the user stays in, dynamically and interactively in real time. Preferably, the environmental parameters and information can be sensed by different sensors, and the real-time location and direction of virtual image corresponded to the real space are calculated accordingly; the display projects or superposes the virtual image onto the actual object in the reality. In addition, when the real environment and virtual environment are two ends of continuous system respectively, the display close to the real environment is also known as Augmented Reality (AR), while the display close to the virtual environment is also known as Virtual Reality (VR); the MR can be regarded as the synthetics of AR and VR.

Figure 2:
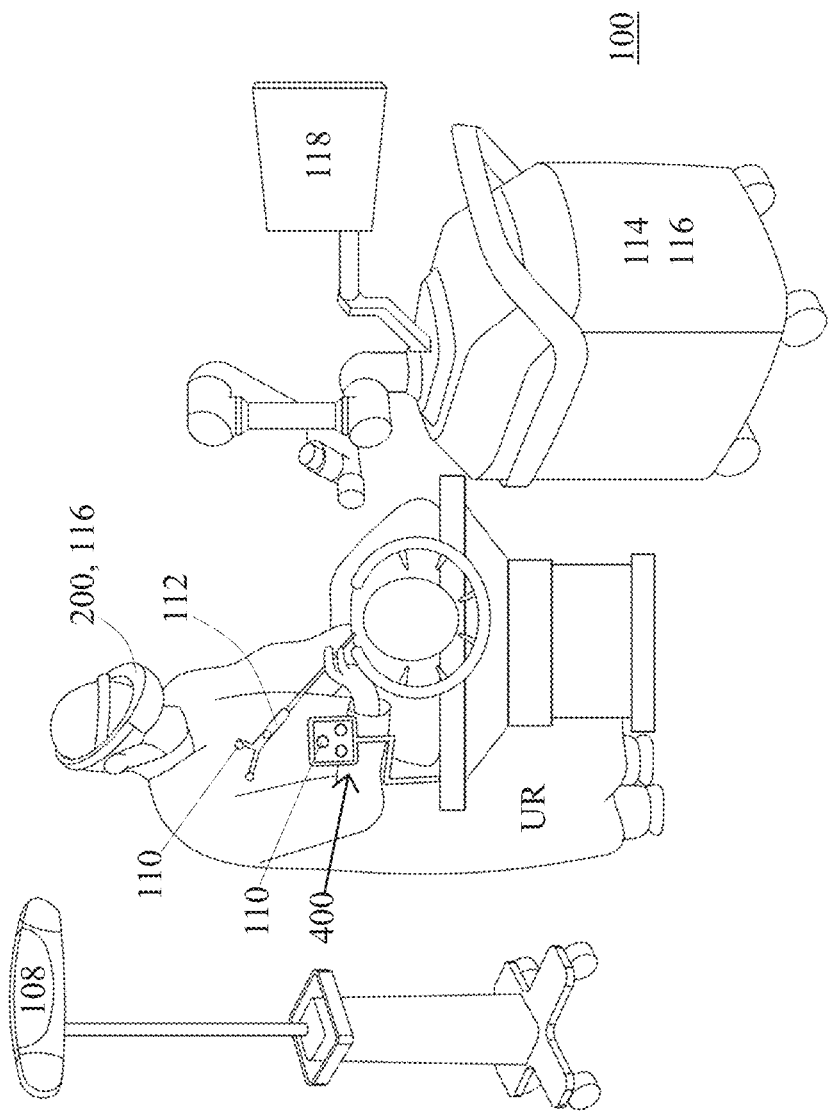
FIG. 2 is a diagram illustrating a fundamental system architecture in a first embodiment for the MR system in accordance with the present invention.
Figure 3:
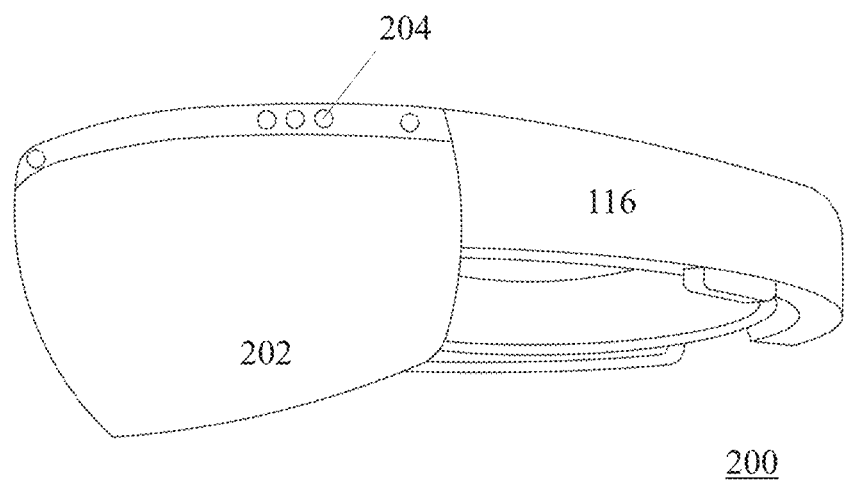
FIG. 3 is a diagram illustrating the MR device included in the system in accordance with the present invention.
Figure 4:
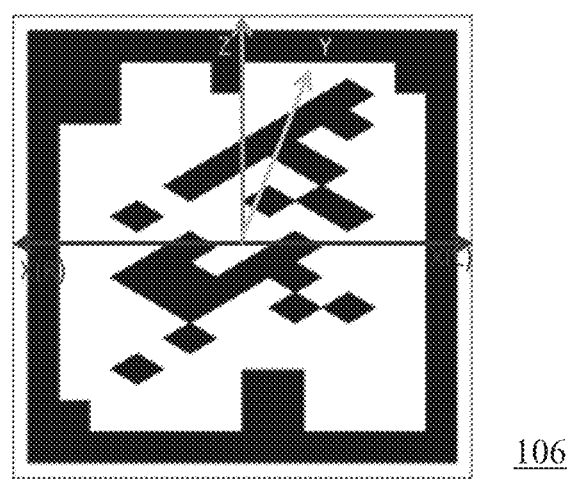
FIG. 4 is a diagram illustrating the positioning marker included in the system in accordance with the present invention.

FIG. 2 is a diagram illustrating a fundamental system architecture in a first embodiment for the MR system in accordance with the present invention. FIG. 3 is a diagram illustrating the MR device included in the system in accordance with the present invention. FIG. 4 is a diagram illustrating the positioning marker included in the system in accordance with the present invention. The MR system 100 in accordance with the present invention includes a MR device 200, a MR display 202, a plurality of MR sensors 204, a registered device 400, a position sensor 108, a group of moveable position markers 110, a surgical instrument 112, a computer 114, a computing unit module 116, and a panel display 118. In this embodiment, the MR device 200 is but not limited to Microsoft HoloLens device, which is able to wear on the head of a user UR, the MR device 200 is for example, a ODG R-7 smart glasses, a Epson Moverio BT-300 smart glasses, an Acer MR glasses, other MR glasses compatible with MS Windows, or other appropriate MR equipments. In this embodiment, the MR display 202 and MR sensor 204 are preferably configured on the same device, i.e. MR device 200, but the MR display 202 and MR sensor 204 can be configured separately. In this embodiment, the computing unit module 116 is preferably configured in the MR device 200, but it can be configured separately from MR device 200, i.e., in computer 114, or in another network computing server.

The MR display 202 is preferably a transparent type, semi-transparent type, or see-through type near to eye device; it can be a panel display, or a curved display. The MR display 202 forms images preferably by but not limited to holographic processing, digital light processing and liquid crystal on silicon. When the MR display 202 displays virtual digital content, the users can see the real scenes, i.e. reality in front of eyes at the same time, like the background behind the virtual digital content. The virtual digital content displayed on the MR display 202 looks like it is superposed on the reality in the users' view. When the digital content displayed on the MR display 202 is related to reality, it seems to be the virtual AR. For example, when different reality messages are perceived by MR sensor 204, after they are processed by the computing unit module 116, the virtual digital content displayed by MR display 202 has different correspondences with the reality, including spatial or temporal correspondence, or performs real-time interaction with the reality, or the virtual model of virtual digital content is combined or connected with the reality, so as to implement different functions and effects of MR.

The MR device 200 is preferably designed and made into a Head-Mounted Display (HMD), or a Head Up Display (HUD), but the form of glasses-like smart glasses is preferred. A plurality of MR sensors 204 are installed on the main body of MR device 200, or on the case, preferably configured in the upper part of main body or in the position corresponding to the forehead, to avoid obstructing the users' sight. A plurality of MR sensors 204 are preferably but not limited to environmental camera, depth camera, light sensor, three primary colors camera (RGB camera), infrared light sensor, IMU, multiaxial accelerometer or range finder, for sensing various reality messages of reality, such as the direction, location, size, distance and ambient brightness of different solid models in the reality, which are transmitted to the computing unit module 116.

For instance, the environmental camera is built in for taking the images of reality around the MR device 200. The depth camera is used for sensing the user's control gestures. The RGB camera is used for sensing the registered device 400 configured with the moveable position markers 110 begin back to the user UR and the positioning marker 106 (not shown in FIG. 2) facing toward the user UR, which the positioning marker 106 contains a 2D pattern code as shown in FIG. 4. When the positioning marker 106 exceeds the sensing range of RGB camera, the IMU and accelerometer jointly detect and determine the tri-axial variation of RGB camera in relation to positioning marker 106, so as to determine the location of MR device 200 in 3D space. The MR device 200 scans the positioning marker 106 continuously, when the users' sight has moved, the present invention uses MR sensor 204 to scan the positioning marker 106, so that the MR device 200 can instantly determine and correctly determine the users' exact position, depth and orientation in relation to surgical area, so as to instantly and dynamically adjust the angle, depth, size and orientation given by the virtual digital content; the displayed virtual digital content can respond to the user's sight variation at any time.

Figure 5:
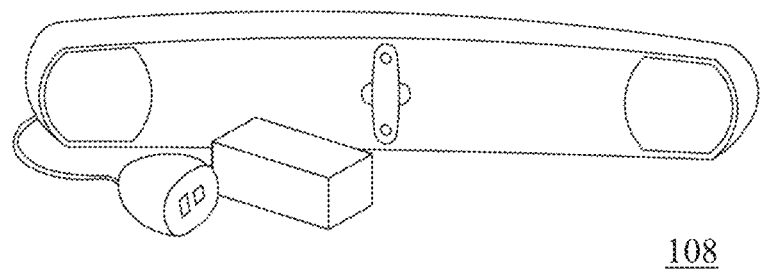
FIG. 5 is a diagram illustrating the position tracker used in the system in accordance with the present invention.
Figure 6:
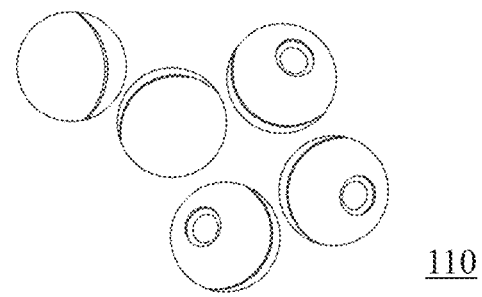
FIG. 6 is a diagram illustrating the moveable position markers used in the system in accordance with the present invention.
Figure 7:
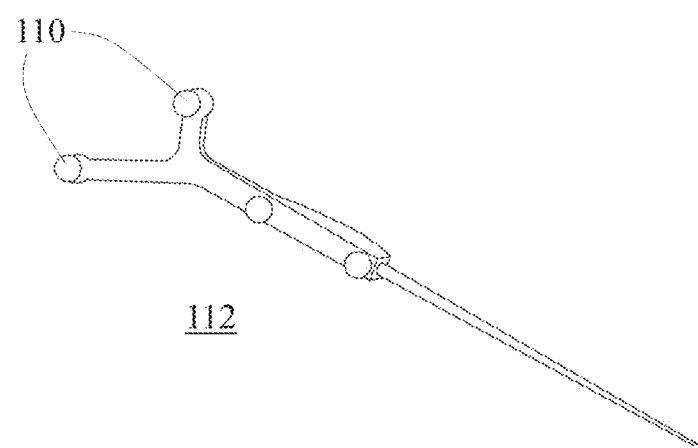
FIG. 7 is a diagram illustrating the surgical instrument equipped with moveable position markers included in the system in accordance with the present invention.

FIG. 5 is a diagram illustrating the position tracker used in the system in accordance with the present invention. FIG. 6 is a diagram illustrating the moveable position markers used in the system in accordance with the present invention. FIG. 7 is a diagram illustrating the surgical instrument equipped with moveable position markers included in the system in accordance with the present invention. The position sensor 108 and moveable position markers 110 coordinate with each other to track current position of different surgical instruments 112. In this embodiment, the position sensor 108 is preferably but not limited to an infrared optical tracker, including an infrared light emitter and a corresponding infrared light detector. The moveable position markers 110 are preferably a corresponding infrared passive reflective marker, designed and made into a sphere in diameter of about 1 cm, which can be embedded in the surgical instrument 112, or an active moveable position marker which emits infrared light. When the infrared scanning of position sensor 108 is actuated, the infrared light reflected by each moveable position markers 110 can be tracked accurately, so as to track current spatial position of each moveable position markers 110 to determine the spatial position of each group of markers formed of multiple moveable position markers 110, which is reported to the system continuously, so that the system can update the real-time spatial position of surgical instrument at any time.

In another embodiment, the position sensor 108 is preferably but not limited to an electromagnetic tracker, including an electromagnetic wave generator and a corresponding electromagnetic field detector. The moveable position markers 110 are preferably the corresponding passive electromagnetic coil marker, when the electromagnetic field scanning of position sensor 108 is actuated, the electromagnetic field magnitude induced by each moveable position markers 110 can be tracked accurately, so as to track current spatial position of each moveable position markers 110.

Figure 8:
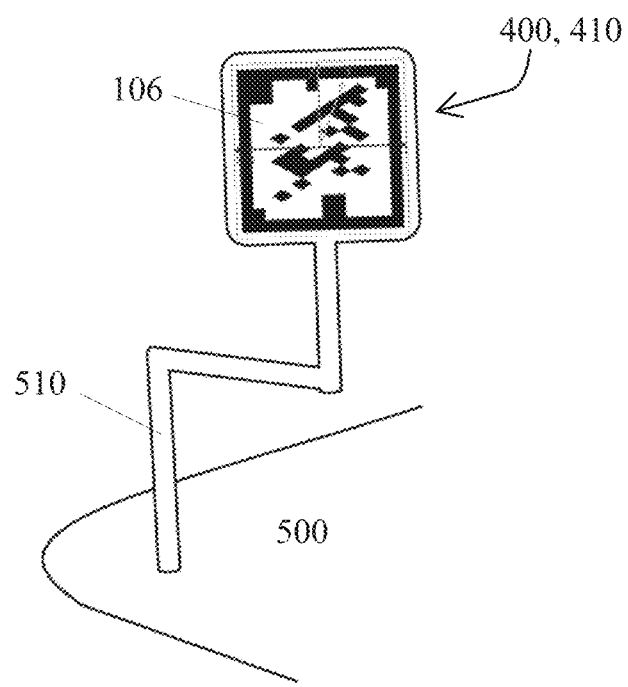
FIG. 8 is a diagram illustrating the front side of the registered device used in the system in accordance with the present invention.
Figure 9:
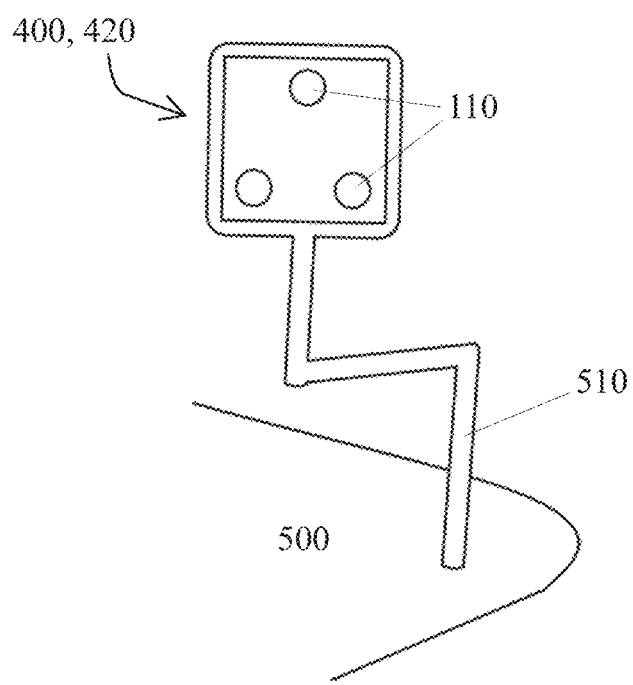
FIG. 9 is a diagram illustrating the back side of the registered device used in the system in accordance with the present invention.

FIG. 8 is a diagram illustrating the front side of the registered device used in the system in accordance with the present invention. FIG. 9 is a diagram illustrating the back side of the registered device used in the system in accordance with the present invention. In order to ensure the correspondence between positioning marker 106 and moveable position markers 110, the moveable position markers 110 and positioning marker 106 by the surgical area are combined in the present invention and fixed to, for example, the front side 410 and back side 420 of a registered device 400, so that a definitely changeless position correlation and an anchored connection relationship are established between positioning marker and moveable position markers. As shown in FIG. 8, a positioning marker 106 with a characteristic pattern in 2D is affixed to the front side 410 of a registered device 400. As shown in FIG. 9, the back side 420 of a registered device 400 is provided with a group of moveable position markers 110. The entire registered device 400 is preferably fixed to, for example, an extension rod 510 secured to, for example, a slidable side rail, configured on an operating table 500.

Therefore, by jointly configuring on the same registered device, the relative position relationships in a 3D space among the positioning marker 106 and multiple moveable position markers 110 are accordingly determined. Typically, the positioning marker 106 and multiple moveable position markers 110 have their own respective coordinate frames which are different from each other and require further coordinate transformations thereamong. When the relative spatial position relationships among positioning marker 106 and multiple moveable position markers 110 are determined, pre-determined, pre-defined, or preset (default), for the MR device 200 and position sensor 108 to detect respectively, through jointly configuring on the same registered device, the surgical area (lesion) coordinate frame detected by the position sensor 108 is able to be sequentially transformed to a moveable position marker coordinate frame through multiple moveable position markers 110, and transformed to a positioning marker coordinate frame through a positioning marker 106. At last, the MR device 200 detects the positioning marker 106 and in the meantime the MR device 200 acquires the exact location of surgical area computed by the computing unit module 116 performing a series of above-mentioned coordinate transformations, so that a virtual digital image model is capable of being aligned and corresponded to the surgical area in the reality.

Figure 10:
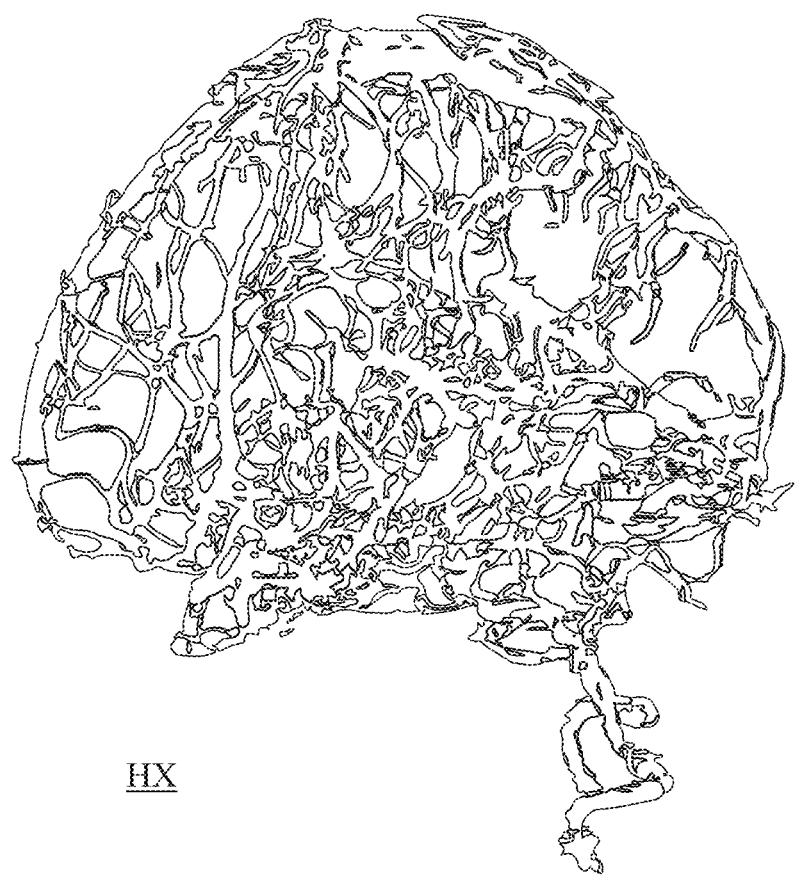
FIG. 10 is a diagram illustrating the 3D digital image model which shows a spatial distribution for blood vessels inside a patient's brain displayed by the MR device and is ready, able to align with the patients' surgical area, and is generated by the system in accordance with the present invention according to patient's multiple CTA images.

FIG. 10 is a diagram illustrating the 3D digital image model which shows a spatial distribution for blood vessels inside a patient's brain displayed by the MR device and is ready, able to align with the patients' surgical area, and is generated by the system in accordance with the present invention according to patient's multiple CTA images. The 3D MR image data of surgical area used by the system can be made by surgical area image reconstruction program module beforehand by data preprocessing independently. The surgical area image reconstruction program module contains a special intelligent algorithm, different see-through slice images, such as X-ray image, CT image, CTA image, DSA image, MIP image and MRI or basic image as MRA can be processed by a series of approaches contained in the intelligent algorithm, such as denoising, image pre-processing, anatomic characteristics recognition, anatomic characteristics enhancement, alignment, collage, interpolation or extrapolation, so as to build a digital space model. When the digital space model preprocessing of surgical area is completed, it is provided for the MR device 200 and aligned to the reality, and then displayed on the patients' surgical area.

In terms of the intelligent algorithm of the present invention, first of all, the vascular image contained in the basic image must be separated or segmented from the image. The blood vessel image segmentation procedure of the present invention provides three main segmentation methods, which are vessel image enhancement, recognition and seed point tracking. The vessel enhancement method is applicable to low noise basic image. The recognition method tracks blood vessels by the region or boundary deformation in different images according to the defined initial region or boundary of blood vessels; it has to perform more complex mathematical calculation. The seed point tracking method judges the blood vessels in other images by the initial seed point position according to previous image, the method does not require too much mathematical operation. The intelligent algorithm of the present invention separates the surgical area information after several vascular image segmentations of different 2D basic images; the 3D digital model of surgical area is built for the surgeons to make accurate planning.

According to the 3D digital image model showing a spatial distribution for blood vessels inside a patient's brain which is constructed by the system in accordance with the present invention as shown in FIG. 10, it is demonstrated that the intelligent algorithm used in the present invention is capable of processing, presenting, and displaying clearly for various critical anatomic characteristics, including the circle of Willis, cerebral artery, cerebral vein and surgical area, e.g.: aneurysm.

Figure 11:
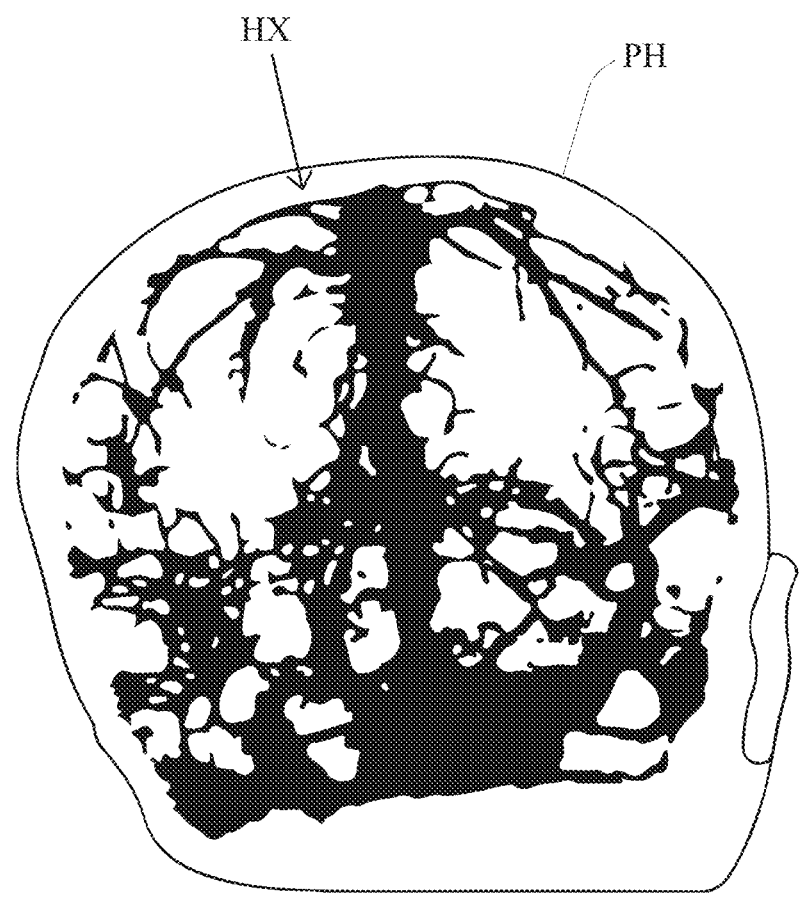
FIG. 11 is diagrams illustrating the overall MR images viewed by the user wearing the MR device and seeing through the MR device in accordance with the present invention.

FIG. 11 is diagrams illustrating the overall MR images viewed by the user wearing the MR device and seeing through the MR device in accordance with the present invention. FIG. 11 mainly shows the MR image displayed by the MR device after the 3D cerebral blood vessel image generated by the system is aligned to the surgical area. The surgical area is the head in this embodiment, so when the users wear the MR device, the visually seen image contains the patients' head PH and the 3D cerebral blood vessel distribution image HX displayed on the glasses after alignment to surgical area. The 3D cerebral blood vessel distribution image HX has been accurately aligned to the surgical area, i.e. the patients' head PH, after system calculation and processing, so the users can see the MR of 3D cerebral blood vessel distribution image HX overlapped on the surgical area directly on the see-through display. The distribution pattern of blood vessels, nerves and tissues in the patients' head PH seen through (before craniotomy) and current condition of lesion or injury can be viewed clearly by MR or AR.

The present invention uses MR technology to display the 3D cerebral blood vessel model and surgical instrument on the patients' head, so that the surgeons know the blood vessel positions around the surgical instrument instantly, thus reducing the possible injury risks. The 3D cerebral blood vessel model is directly projected on the patients' skull by using MR technology, intuitively providing the distribution of complex blood vessels in the surgical area for the surgeons. With X-ray image mapping applied to aneurysmal embolization surgery, the guide wire can reach the surgical area more easily and safely. The present invention uses 3D image data for surgical navigation, and also uses 2D image data for surgical navigation.

Figure 12:
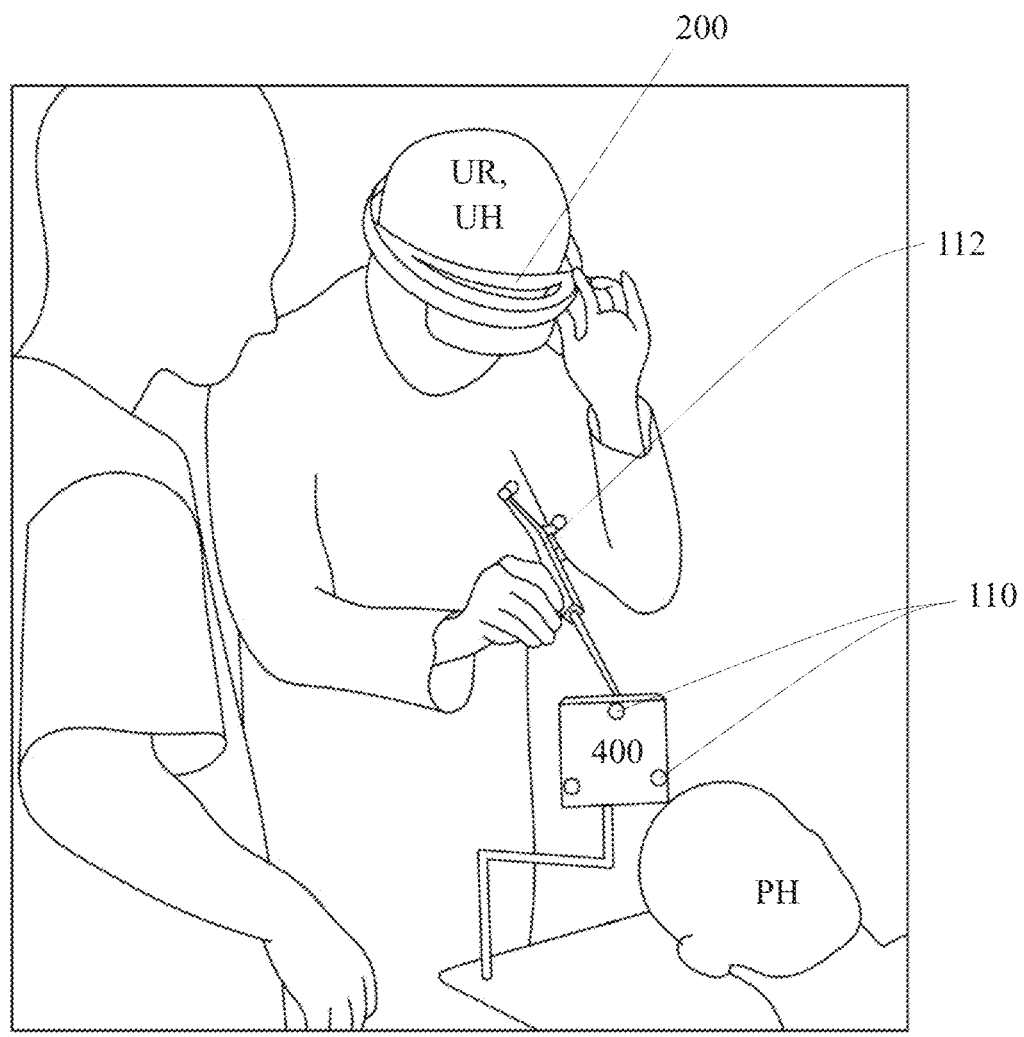
FIG. 12 is a diagram illustrating the actual scenario showing the operation for the surgical navigation system in accordance with the present invention.
Figure 13:
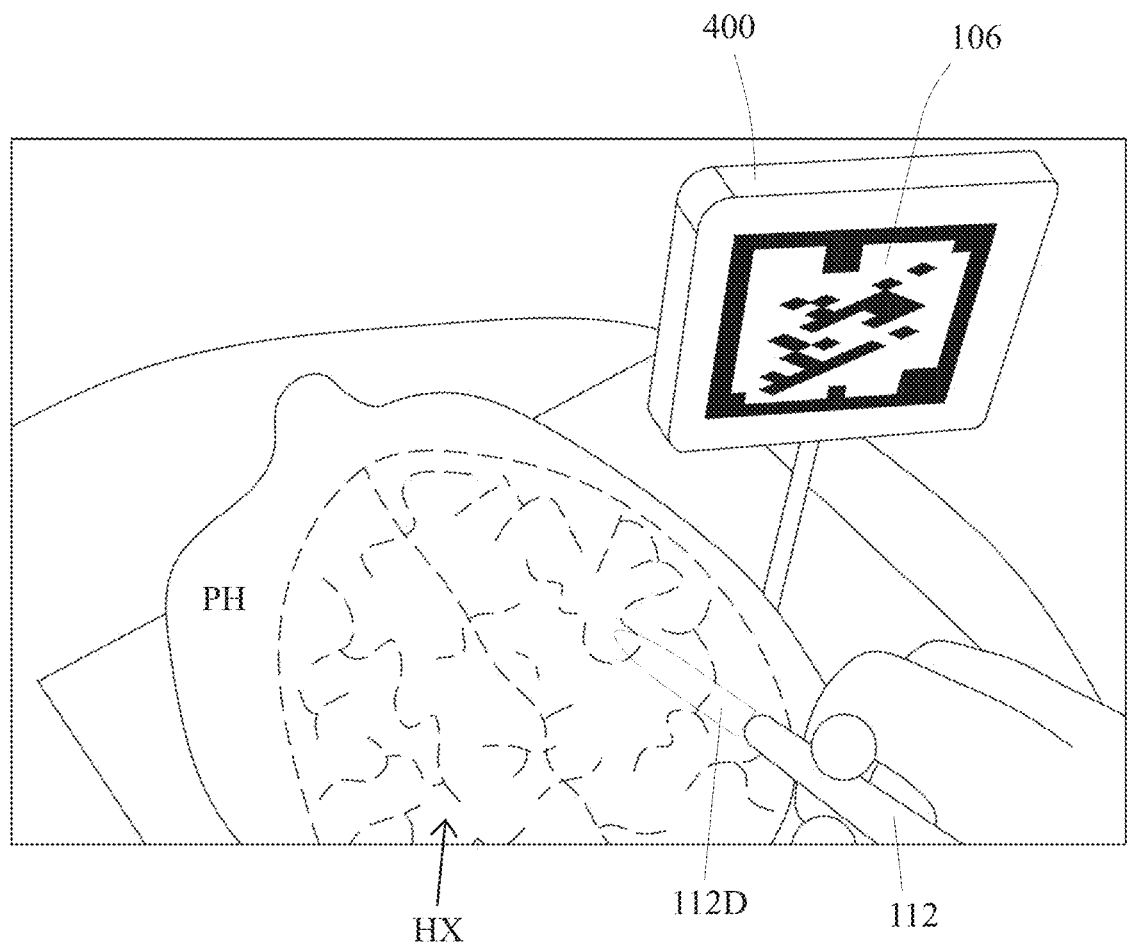
FIG. 13 is a diagram illustrating the actual scenario seen by the user in FIG. 12 through the head-worn MR device.
Figure 14:
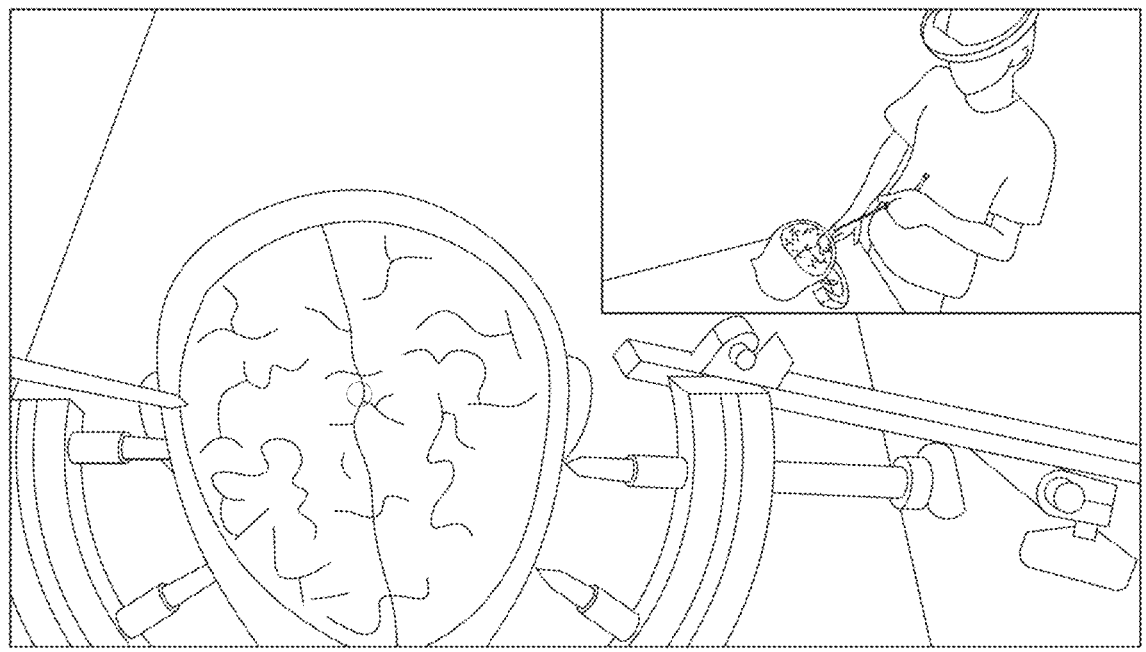
FIG. 14 is a diagram illustrating the actual scenario showing a 3D brain digital model that is aligned the corresponding skull and displayed by the MR device in accordance with the present invention.

FIG. 12 is a diagram illustrating the actual scenario showing the operation for the surgical navigation system in accordance with the present invention. FIG. 13 is a diagram illustrating the actual scenario seen by the user in FIG. 12 through the head-worn MR device. FIG. 14 is a diagram illustrating the actual scenario showing a 3D brain digital model that is aligned the corresponding skull and displayed by the MR device in accordance with the present invention. In FIG. 12, it discloses that during the practical application of the system, the user UR can wear the MR device 200 on the user's head UH, the user grips a surgical instrument 112 in right hand, eyes on the patient's head PH, a registered device 400 is placed by the patient's head PH; the front and back sides of registered device 400 are equipped with positioning marker 106 and moveable position markers 110 respectively, for the MR device 200 and position sensor 108 to read respectively. The user can see the surgical instrument 112 in right hand and patient's head PH through the MR device 200, but the MR device 200 displays a digital space image model HX corresponding to the patient's head PH, containing brain tissue and digital surgical instrument 112D in this embodiment, on the patient's head PH. The user can see the MR image on MR device 200, as shown in FIG. 13, the overlap of digital surgical instrument 112D and the surgical instrument 112 in the patient's head PH can be observed in FIG. 14.

Figure 15:
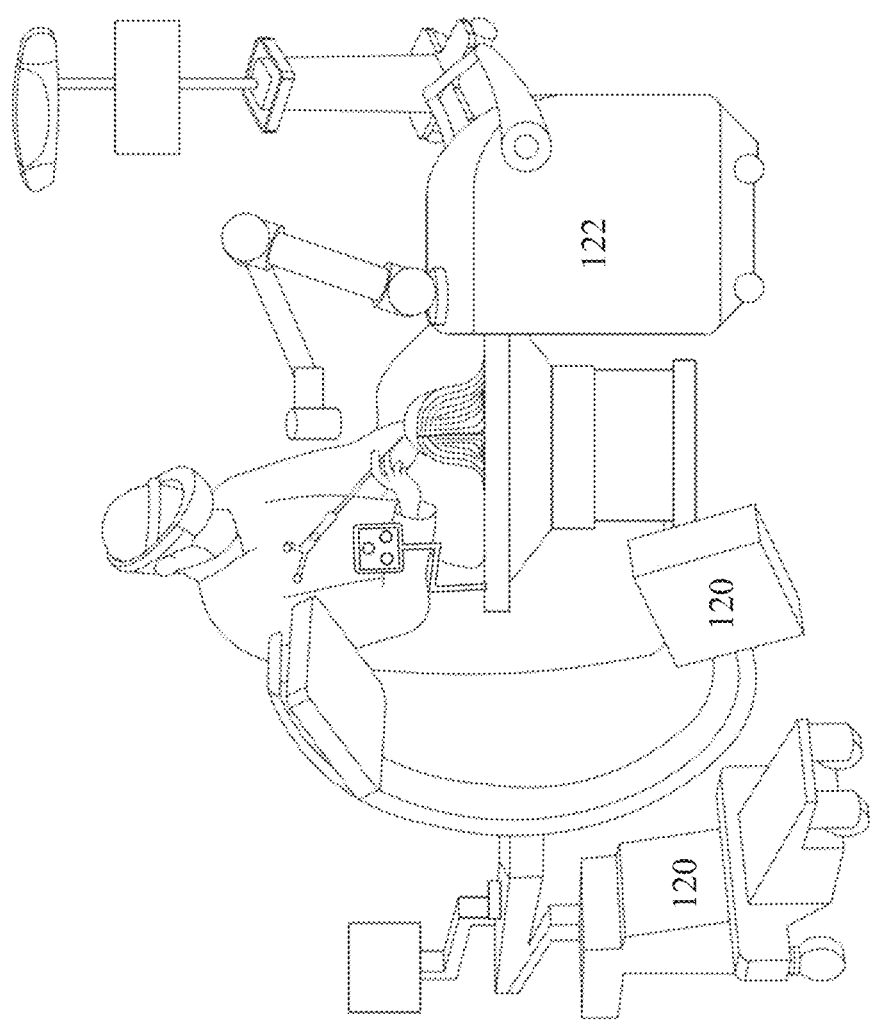
FIG. 15 is a diagram illustrating a fundamental system architecture in a second embodiment for the MR system in accordance with the present invention.

FIG. 15 is a diagram illustrating a fundamental system architecture in a second embodiment for the MR system in accordance with the present invention. When the system is used in a practical surgery, a C-arm X-ray machine and a robotic surgical auxiliary equipment can be applied to assist surgery. The mixed reality system 100 of the present invention in this embodiment has a C-arm X-ray machine 120 and a robot surgical auxiliary equipment 122 based on the first embodiment. The C-arm X-ray machine 120 preferably takes the latest see-through image of surgical area according to the surgical procedure and requirement, and updates the digital space image model displayed by MR device instantly. With the C-arm X-ray machine 120, the system can provide real-time dynamic digital space image model of surgical area for the user in the course of operation. When the robotic surgical auxiliary equipment 122, especially robot arm, is combined with the real-time dynamic digital space image model generated by the present invention, the surgical stability and precision are enhanced greatly for the user, especially applicable to different minimally invasive surgeries.

Figure 16:
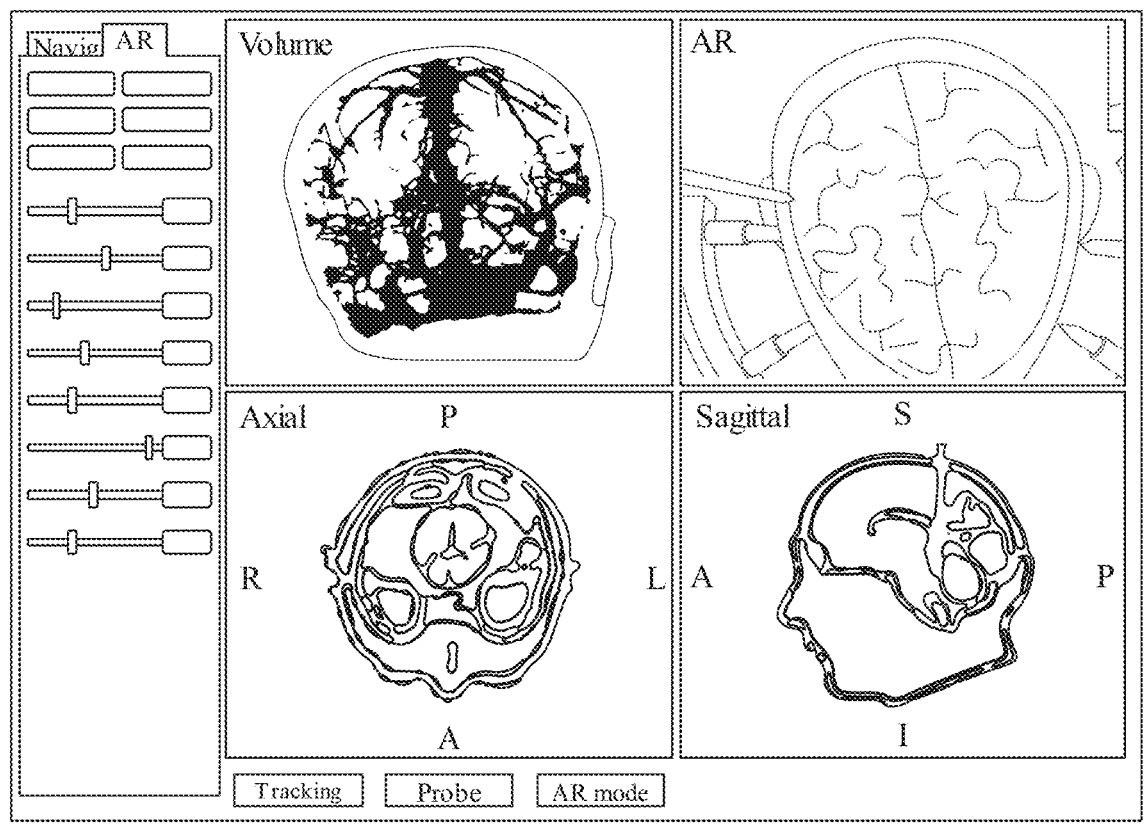
FIG. 16 is a diagram illustrating a computer-aided surgical planning system (CASP) which applies the 3D digital image model information generated by the system in accordance with the present invention.

FIG. 16 is a diagram illustrating a computer-aided surgical planning system (CASP) which applies the 3D digital image model information generated by the system in accordance with the present invention. The digital space image model generated by the system, including the model information of 3D cerebral blood vessel distribution, can be directly used as computer-aided surgical planning system (CASP), or the model information can be provided for the conventional computer-aided surgical planning and navigation system, conventional preoperative planning software or conventional preoperative planning system, as shown in FIG. 16.

In recent years, with the development of image-aided surgical navigation system, for example, the image-aided surgical navigation system is admitted to the brain, joint and vertebrae surgeries. Taking the surgical navigation system for brain as an example, the surgeon is provided with real-time relative positions of surgical instrument, brain CT image and surgical area, but the surgeon is still unaware of intuitive relationship between navigation information and surgical area. Based on these systems, the surgeon only directly sees the tissue surface layer of surgical site, and watches the navigation system on the screen to check the relationships among instrument, patient and surgical area, he cannot intuitively predict the important blood vessels, nerves or other tissues which must be evaded under the tissue surface layer. In the case of puncture sampling, drainage or electrocauterization surgery, the safe path for inserting the instrument in the brain shall be planned.

In conventional brain surgery, the surgeons analyze brain tissue structure and plans appropriate surgical approach only according to preoperative images, including CT, MRI and CTA, as well as clinical experience. However, if the cerebral arteries are injured in the process, there will be intracranial hemorrhage, severe sequelae even death of the patient. The present invention combines image-guided surgical navigation system, blood vessel/nerve segmentation and reconstruction system and MR system, the MR/AR glasses project the 3D image model of surgical instrument/blood vessels/nerves/surgical area on the patient by real-time 3D visualization, providing relative spatial position information of surgical area and surgical instrument, assisting the surgeons to plan a safe surgical approach more intuitively, the 3D surgical navigation is performed, so as to reduce the risks of brain surgery.

The present invention can reduce the risks of brain surgery and the radiation and shorten the surgical time, so that the surgeons are more intuitive during the surgery. The CT, CTA, MRI, MRA or DTI images are obtained by preoperative scanning, so as to build the 3D digital model of brain tissue and surgical area. With the computer technology, image processing techniques and positioning system, the MR/AR glasses align the images of surgical instrument, lesions and such brain tissues as cerebral blood vessels, cranial nerves and sulcus and display them on the patients. The surgeons can plan the surgical approach more intuitively according to the observed spatial position relation between brain tissue and lesion before surgery. The surgeons can obtain the real-time relative position relation information of surgical instrument, lesion and patients in the course of operation, so as to make favorable judgment. The surgery can be done safely and rapidly. The wound is smaller and the brain is less damaged after surgery, the rehabilitation time is shortened.

The complete set of surgical navigation system proposed by the present invention includes medical image segmentation and reconstruction operation of C-arm X-ray machine and CT, an Optic Tracker, a plurality of positioning marker modules, a traceable surgical instrument, a navigation computer, a robot surgical assistive equipment, multiple MR/AR wearable equipments (Microsoft Hololens), as well as such auxiliary equipments as a 3D printing equipment, a panel display and multiple fixers.

The navigation system of the present invention can coordinate with the existing 2D/3D C-arm X-ray equipment and surgical instrument of hospital, the self-developed navigation software is integrated with MR/AR, Robot, optic tracker and computer to assist the surgeons with accurate surgical positioning and navigation. This navigation system has the following effects: (1) the number of X-ray images captured during operation is reduced a lot, (2) the time of minimally invasive surgery and anaesthesia is shortened, (3) the surgical accuracy and success rate are enhanced, (4) the minimally invasive brain surgery is easier, (5) preoperative planning and simulation, (6) the patients can take part in preoperative explanation, promoting surgeon-patient communication.

There are further embodiments provided as follows.

Embodiment 1: A mixed reality system integrated with a surgical navigation system includes: a group of moveable position markers configured on a surgical instrument; a position sensor sensing the group of moveable position markers to acquire an instrument coordinate for the surgical instrument; a registered positioning marker configured in proximity to a surgical area to acquire a surgical area coordinate for the surgical area; a plurality of mixed reality sensors detecting the registered positioning marker and a plurality of mixed reality information; a computing unit module configured to receive the instrument coordinate, the surgical area coordinate, the plurality of mixed reality information, and a digital model of the surgical area, to render the digital model corresponded to the surgical area, and to add a digital instrument object into the digital model in accordance with the instrument coordinate; and a mixed reality display providing for a user to view and showing the digital model and the digital instrument object to the user upon the receipt thereof.

Embodiment 2: The mixed reality system in Embodiment 1, further includes one of images as follows: an X-ray image, a computer tomography image, a computer tomography angiography image, a digital subtraction angiography image, a maximum intensity projection image, a diffusion tensor image, a nuclear magnetic resonance image, or a nuclear magnetic resonance angiography image; a computer selectively including the computing unit module; a surgical area image reconstruction module including an intelligent computing algorithm configured to execute by the computing unit module selectively to generate the digital model of the surgical area; a robot-assisted surgery equipment configured to assist the user to perform a surgery; and a display panel receiving and showing digital contents provided by the computer.

Embodiment 3: In the mixed reality system in Embodiment 1, the digital model of the surgical area is pre-constructed based on one of an X-ray image, a computer tomography image, a computer tomography angiography image, a digital subtraction angiography image, a maximum intensity projection image, a diffusion tensor imaging image, a nuclear magnetic resonance image, a nuclear magnetic resonance angiography image, and a combination thereof by executing an intelligent computing algorithm, and the intelligent computing algorithm include one of a noise removal processing, a feature identification processing, a feature enhancement processing, an alignment processing, a stitch processing, in interpolation processing, an extrapolation processing, and a combination thereof.

Embodiment 4: In the mixed reality system in Embodiment 1, the digital model of the surgical area is one of a two-dimension digital image of the surgical area, a three-dimension digital image of the surgical area, and a combination thereof.

Embodiment 5: In the mixed reality system in Embodiment 1, the plurality of mixed reality sensors and the mixed reality display are configured on the same one device, or each of the plurality of mixed reality sensors and the mixed reality display are configured on separate devices respectively.

Embodiment 6: In the mixed reality system in Embodiment 1, the computing unit module, the plurality of mixed reality sensors and the mixed reality display are configured on the same one device, the computing unit module and the plurality of mixed reality sensors are configured on the same one device, the computing unit module and the mixed reality display are configured on the same one device, the computing unit module, the plurality of mixed reality sensors and the mixed reality display are configured on separate devices respectively, the computing unit module and the plurality of mixed reality sensors are configured on separate devices respectively, or the computing unit module and the mixed reality display are configured on separate devices respectively.

Embodiment 7: In the mixed reality system in Embodiment 1, the plurality of mixed reality sensors are selected from a surrounding camera, a depth camera, a light sensor, a RGB camera, an infra-ray camera, an inertia measurement unit, a multi-axis accelerometer, a rangefinder, and a combination thereof.

Embodiment 8: In the mixed reality system in Embodiment 1, the position sensor is an infra-ray tracker or an electromagnetic tracker, the group of moveable position markers are an infra-ray reflective marker or a coil winding marker and provides for configuring on the surgical instrument, and the registered positioning marker includes a two-dimension code pattern.

Embodiment 9: In the mixed reality system in Embodiment 1, the plurality of mixed reality sensors and the mixed reality display are configured on the same one mixed reality device, and the mixed reality device is a Microsoft Hololens device, an ODG R-7 smart glass, an Epson Moverio BT-300 smart glass, or an Acer mixed reality glass.

Embodiment 10: The mixed reality system in Embodiment 1, further includes one of devices as follows: a registered device configured in proximity to a surgical area and having a first surface and a second surface fixed with the first surface wherein the first surface provides for the positioning marker to configure and the second surface provides for the group of moveable position markers to configure, and while the registered device is placed the relative positions of the positioning marker and the group of moveable position markers with respect to the surgical area are determined accordingly; and a platform configured in proximity to a surgical area and having a plurality of surfaces wherein one of the plurality of surfaces provides for the group of moveable position markers to configure and the others of the plurality of surfaces provides for a plurality of the positioning markers to configure, and while the platform is placed the relative positions of the plurality of the positioning markers and the group of moveable position markers with respect to the surgical area are determined accordingly.

While the disclosure has been described in terms of what are presently considered to be the most practical and preferred embodiments, it is to be understood that the disclosure need not be limited to the disclosed embodiments. On the contrary, it is intended to cover various modifications and similar arrangements included within the spirit and scope of the appended claims, which are to be accorded with the broadest interpretation so as to encompass all such modifications and similar structures. Therefore, the above description and illustration should not be taken as limiting the scope of the present disclosure which is defined by the appended claims.

What is claimed is:

1. A mixed reality system integrated with a surgical navigation system, comprising:
   a group of moveable position markers configured on a surgical instrument;
   a registered device having a first surface configured with a registered positioning marker and a second surface opposite to the first surface configured with a part of the group of moveable position markers and configured in proximity to a surgical area to acquire a surgical area coordinate for the surgical area;
   a plurality of mixed reality sensors detecting the registered positioning marker and a plurality of mixed reality information;
   a position sensor disposed separately away from the plurality of mixed reality sensors, having a line-of-sight direction substantively opposite from these of the plurality of mixed reality sensors, and sensing the group of moveable position markers to acquire an instrument coordinate for the surgical instrument;
   a computing unit module configured to receive the instrument coordinate, the surgical area coordinate, the plurality of mixed reality information, and a digital model of the surgical area, to render the digital model corresponded to the surgical area, and to add a digital instrument object into the digital model in accordance with the instrument coordinate; and
   a mixed reality display providing for a user to view and showing the digital model and the digital instrument object to the user upon the receipt thereof.

2. The mixed reality system as claimed in claim 1, further comprising one of devices as follows:
   a C-arm imaging machine providing for forming an X-ray image, a computer tomography image, a computer tomography angiography image, a digital subtraction angiography image, a maximum intensity projection image, a diffusion tensor imaging image, a nuclear magnetic resonance imaging image, or a nuclear magnetic resonance angiography image;
   a computer selectively including the computing unit module;
   a surgical area image reconstruction module including an intelligent computing algorithm configured to execute by the computing unit module selectively to generate the digital model of the surgical area;
   a robot-assisted surgery equipment configured to assist the user to perform a surgery; and
   a display panel receiving and showing digital contents provided by the computer.

3. The mixed reality system as claimed in claim 1, wherein the digital model of the surgical area is pre-constructed based on one of an X-ray image, a computer tomography image, a computer tomography angiography image, a digital subtraction angiography image, a maximum intensity projection image, a diffusion tensor imaging image, a nuclear magnetic resonance imaging image, a nuclear magnetic resonance angiography image, and a combination thereof by executing an intelligent computing algorithm, and the intelligent computing algorithm include one of a noise removal processing, a feature identification processing, a feature enhancement processing, an alignment processing, a stitch processing, in interpolation processing, an extrapolation processing, and a combination thereof.

4. The mixed reality system as claimed in claim 1, wherein the digital model of the surgical area is one of a two-dimension digital image of the surgical area, a three-dimension digital image of the surgical area, and a combination thereof.

5. The mixed reality system as claimed in claim 1, wherein the plurality of mixed reality sensors and the mixed reality display are configured on the same one device, or each of the plurality of mixed reality sensors and the mixed reality display are configured on separate devices respectively.

6. The mixed reality system as claimed in claim 1, wherein the computing unit module, the plurality of mixed reality sensors and the mixed reality display are configured on the same one device, the computing unit module and the plurality of mixed reality sensors are configured on the same one device, the computing unit module and the mixed reality display are configured on the same one device, the computing unit module, the plurality of mixed reality sensors and the mixed reality display are configured on separate devices respectively, the computing unit module and the plurality of mixed reality sensors are configured on separate devices respectively, or the computing unit module and the mixed reality display are configured on separate devices respectively.

7. The mixed reality system as claimed in claim 1, wherein the plurality of mixed reality sensors are selected from a surrounding camera, a depth camera, a light sensor, a RGB camera, an infra-ray camera, an inertia measurement unit, a multi-axis accelerometer, a rangefinder, and a combination thereof.

8. The mixed reality system as claimed in claim 1, wherein the position sensor is an infra-ray tracker or an electromagnetic tracker, the group of moveable position markers are an infra-ray reflective marker, an infra-ray emission marker, or a coil winding marker and provides for configuring on the surgical instrument, and the registered positioning marker includes a two-dimension code pattern.

9. The mixed reality system as claimed in claim 1, wherein the plurality of mixed reality sensors and the mixed reality display are configured on the same one mixed reality device, and the mixed reality device is a Microsoft Hololens device, an ODG R-7 smart glass, an Epson Moverio BT-300 smart glass, an Epson Moverio Pro BT-2000 smart glass, a Magic Leap One, or an Acer mixed reality glass.

10. The mixed reality system as claimed in claim 1, further comprising one of devices as follows:
   a registered device configured in proximity to a surgical area and having a first surface and a second surface fixed with the first surface wherein the first surface provides for the positioning marker to configure and the second surface provides for the group of moveable position markers to configure, and when the registered device is settled, the relative positions of the positioning marker and the group of moveable position markers with respect to the surgical area are determined accordingly; and
   a registered platform configured in proximity to a surgical area and having a plurality of surfaces wherein one of the plurality of surfaces provides for the group of moveable position markers to configure and the others of the plurality of surfaces provides for a plurality of the positioning markers to configure, and when the platform is settled, the relative positions of the plurality of the positioning markers and the group of moveable position markers with respect to the surgical area are determined accordingly.

* * * * *